US00PP25234P2

(12) United States Plant Patent
Misato

(10) Patent No.: US PP25,234 P2
(45) Date of Patent: Jan. 20, 2015

(54) *MANDEVILLA* PLANT NAMED 'SUNPARARE 15'

(50) Latin Name: *Mandevilla hybrida*
Varietal Denomination: Sunparare 15

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 123 days.

(21) Appl. No.: 13/815,179

(22) Filed: Feb. 5, 2013

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Sunparare 15', characterized by its upright and vining plant habit; vigorous growth habit; freely branching habit, dense and bushy plant form; dark green-colored leaves; freely flowering habit; long flowering period; and large bright red-colored flowers.

1 Drawing Sheet

Botanical designation: *Mandevilla hybrida.*
Cultivar denomination: 'SUNPARARE 15'.

BACKGROUND OF THE INVENTION

The present invention relates to a new and distinct cultivar of *Mandevilla* plant, botanically known as *Mandevilla hybrida* and hereinafter referred to by the name 'Sunparare 15'.

The new *Mandevilla* plant is a product of a planned breeding program conducted by the Inventor in Higashiomi, Shiga, Japan. The objective of the breeding program is to create new freely-branching and vining *Mandevilla* plants with numerous large attractive flowers.

The new *Mandevilla* plant originated from a cross-pollination in Higashiomi, Shiga, Japan in April, 2006 of a proprietary selection of *Mandevilla hybrida* identified as code number M37-1, not patented, as the female, or seed parent with a proprietary selection of *Mandevilla hybrida* identified as code number MH-3, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2009.

Asexual reproduction of the new *Mandevilla* plant by cuttings in Higashiomi, Shiga, Japan since October, 2009 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparare 15'.

These characteristics in combination distinguish 'Sunparare 15' as a new and distinct *Mandevilla* plant:

1. Upright and vining plant habit.
2. Vigorous growth habit.
3. Freely branching habit, dense and bushy plant form.
4. Dark green-colored leaves.
5. Freely flowering habit.
6. Long flowering period.
7. Large bright red-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* are more vigorous than plants of the female parent selection.
2. Plants of the new *Mandevilla* have shorter internodes than plants of the female parent selection.
3. Plants of the new *Mandevilla* and the female parent selection differ in flower color as plants of the female parent selection have slightly darker red-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are more vining than and are not as compact as plants of the male parent selection.
2. Plants of the new *Mandevilla* and the male parent selection differ in flower color as plants of the male parent selection have red purple-colored flowers.

Plants of the new *Mandevilla* can be compared to plants of the *Mandevilla* 'Sunparacore', disclosed in U.S. Plant Pat. No. 23,959. In side-by-side comparisons conducted in Higashiomi, Shiga, Japan, plants of the new *Mandevilla* differed from plants of 'Sunparacore' in the following characteristics:

1. Plants of the new *Mandevilla* had longer lateral branches than plants of 'Sunparacore'.

2. Plants of the new *Mandevilla* had shorter internodes than plants of 'Sunparacore'.
3. Plants of the new *Mandevilla* had elliptical-shaped leaves whereas plants of 'Sunparacore' had obovate-shaped leaves.
4. Plants of the new *Mandevilla* had larger flowers than plants of 'Sunparacore'.
5. Plants of the new *Mandevilla* and 'Sunparacore' differed in flower color as plants of 'Sunparacore' had dark red-colored flowers.
6. Plants of the new *Mandevilla* had longer and thicker peduncles than plants of 'Sunparacore'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparare 15' grown in a container.

The photograph at the bottom of the sheet is a close-up view of a typical flowering plant of 'Sunparare 15'.

DETAILED BOTANICAL DESCRIPTION

The aforementioned photographs and following observations, measurements and values describe plants grown during the late summer and early autumn in 18-cm containers in an outdoor nursery in Higashiomi, Shiga, Japan and under cultural practices typical of commercial production. During the production of the plants, day temperatures averaged 25° C. and night temperatures averaged 15° C. Plants were five months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparare 15'.

Parentage:

*Female, or seed, parent*.—Proprietary selection of *Mandevilla hybrida* identified as code number M37-1, not patented.

*Male, or pollen, parent*.—Proprietary selection of *Mandevilla hybrida* identified as code number MH-3, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Upright and vining plant habit; vigorous growth habit; freely branching habit.

*Lateral branch description*.—Length: About 154 cm. Diameter: About 2 mm. Internode length: About 2 cm. Strength: Strong. Texture: Smooth, glabrous. Color: Close to 144B.

Foliage description:

*Arrangement*.—Opposite, simple.

*Length*.—About 5.8 cm.

*Width*.—About 3.3 cm.

*Shape*.—Elliptical.

*Apex*.—Acute.

*Base*.—Obtuse.

*Margin*.—Entire.

*Texture, upper and lower surfaces*.—Smooth, glabrous.

*Venation pattern*.—Pinnate, reticulate.

*Color*.—Developing leaves, upper surface: Close to 144A. Developing leaves, lower surface: Close to 144B. Fully expanded leaves, upper surface: Close to 137A; venation, close to 144A. Fully expanded leaves, lower surface: Close to 137D; venation, close to 143D.

*Petiole length*.—About 1.4 cm.

*Petiole diameter*.—About 1.4 mm.

*Petiole texture, upper and lower surfaces*.—Smooth, glabrous.

*Petiole color, upper and lower surfaces*.—Close to 144B.

Flower description:

*Flower type and habit*.—Single salverform flowers arranged in axillary racemes; flowers face upright to outwardly; freely flowering habit with about three to five flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—Slightly fragrant, pleasant.

*Inflorescence height*.—About 12.8 cm.

*Inflorescence diameter*.—About 12 cm.

*Flowers*.—Appearance: Salverform; flared trumpet, corolla fused and five-parted; flowers roughly star-shaped. Diameter: About 8.7 cm. Depth (length): About 7.6 cm. Throat diameter: About 2 cm. Tube length: About 5.1 cm. Tube diameter, mid-section: About 1 cm. Tube diameter, base: About 3.6 mm.

*Flower buds*.—Height: About 6.5 cm. Diameter: About 1.3 cm. Shape: Lenticular. Color: Towards the apex, close to 53C; mid-section, close to 4C; base, close to 180B.

*Corolla*.—Quantity and arrangement: Five petals arranged in a single whorl and fused towards the base into an elongated tube. Petal lobe length: About 3.5 cm. Petal lobe width: About 3.3 cm. Petal lobe shape: Obovate. Petal lobe apex: Mostly obtuse. Petal lobe margin: Entire. Petal lobe texture, upper and lower surfaces: Smooth, glabrous. Throat texture: Smooth, glabrous. Tube texture: Smooth, glabrous. Color: Petal lobe, when opening, upper surface: Close to 45B. Petal lobe, when opening, lower surface: Close to 46B. Petal lobe, fully opened, upper surface: Close to 46B. Petal lobe, fully opened, lower surface: Close to 53B. Throat: Towards the petal, close to 47A and 30A; mid-section and towards the base, close to N52B. Tube: Towards the apex, close to 51A; mid-section, close to 1D; towards the base, close to N34C.

*Calyx*.—Quantity and arrangement: Five sepals arranged in a single whorl; calyx, star-shaped. Sepal length: About 6.6 mm. Sepal width: About 2.7 mm.

Sepal shape: Deltoid. Sepal apex: Acute. Sepal base: Truncate. Sepal margin: Entire. Sepal texture, upper and lower surfaces: Smooth, glabrous. Sepal color: When developing, upper surface: Close to 144A. When developing, lower surface: Close to 144B. Fully developed, upper and lower surfaces: Close to 144C.

*Peduncles*.—Length: About 3.5 cm. Diameter: About 2.3 mm. Texture: Smooth, glabrous. Aspect: Upright to outwardly. Color: Close to 146B.

*Pedicels*.—Length: About 1.7 cm. Diameter: About 2.1 mm. Texture: Smooth, glabrous. Aspect: Obliquely upright. Color: Close to 144A.

*Reproductive organs*.—Stamens: Quantity and arrangement: Typically five; filaments fused to corolla; anthers, connivent. Anther shape: Ellipsoidal. Anther size: About 1.5 mm by 8.5 mm. Anther color: Close to 10C. Pollen amount: Moderate. Pollen color: Close to 4D. Pistils: Quantity: Typically one. Pistil length: About 2.5 cm. Style color: Close to 145D. Stigma shape: Conical. Stigma color: Close to 144C. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparare 15' as illustrated and described.

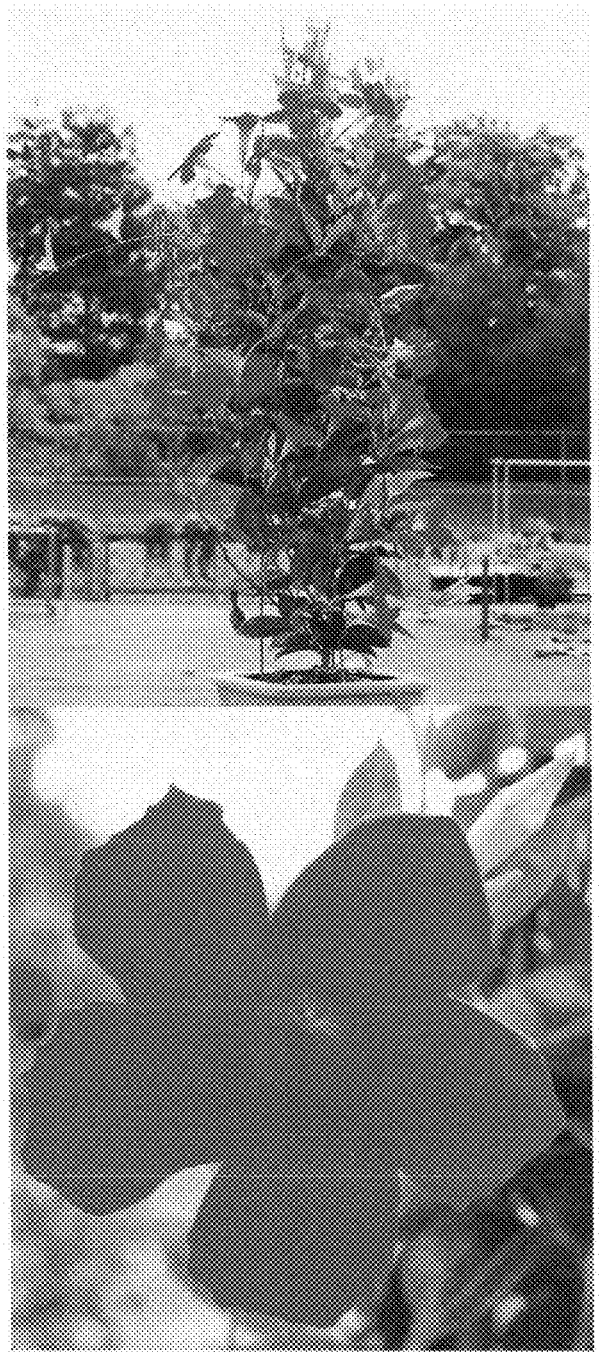

* * * * *